United States Patent [19]
Jacob et al.

[11] Patent Number: 5,084,048
[45] Date of Patent: Jan. 28, 1992

[54] IMPLANT FOR VERTEBRAE WITH SPINAL STABILIZER

[75] Inventors: Hilaire Jacob, Winterthur; Yoshinori Suezawa, Binz; Adam Schreiber, Küsnacht; Rudolf Koch, Berlingen, all of Switzerland

[73] Assignee: Sulzer Brothers Limited, Winterthur, Switzerland

[21] Appl. No.: 546,259

[22] Filed: Jun. 29, 1990

[30] Foreign Application Priority Data
Jul. 12, 1989 [CH] Switzerland .......................... 2610/89

[51] Int. Cl.$^5$ ............................................... A61F 5/04
[52] U.S. Cl. ........................................... 606/61; 623/17
[58] Field of Search ................. 623/11, 16, 17; 606/61

[56] References Cited
U.S. PATENT DOCUMENTS
4,946,458 8/1990 Harms et al. ..................... 623/17

FOREIGN PATENT DOCUMENTS
0240034 10/1987 European Pat. Off. .
8816233 7/1989 Fed. Rep. of Germany .
2615095 11/1988 France .
87/01026 2/1987 World Int. Prop. O. .

Primary Examiner—Randy C. Shay
Attorney, Agent, or Firm—Kenyon & Kenyon

[57] ABSTRACT

The vertebrae implant has a stabilizing element which is articulated to a pair of bone screws so as to accommodate skew positions of the bone screws relative to each other. A slotted clamp is provided to secure the stabilizing element to each bone screw. In addition, each clamp is disposed between a shoulder having a spherical surface and a clamping nut. A washer is also disposed between the clamping nut and the clamp. The clamping nut and/or washer is provided with a spherical surface to provide for pivoting of the clamp relative to the bone screw prior to tightening of the clamping nut.

17 Claims, 3 Drawing Sheets

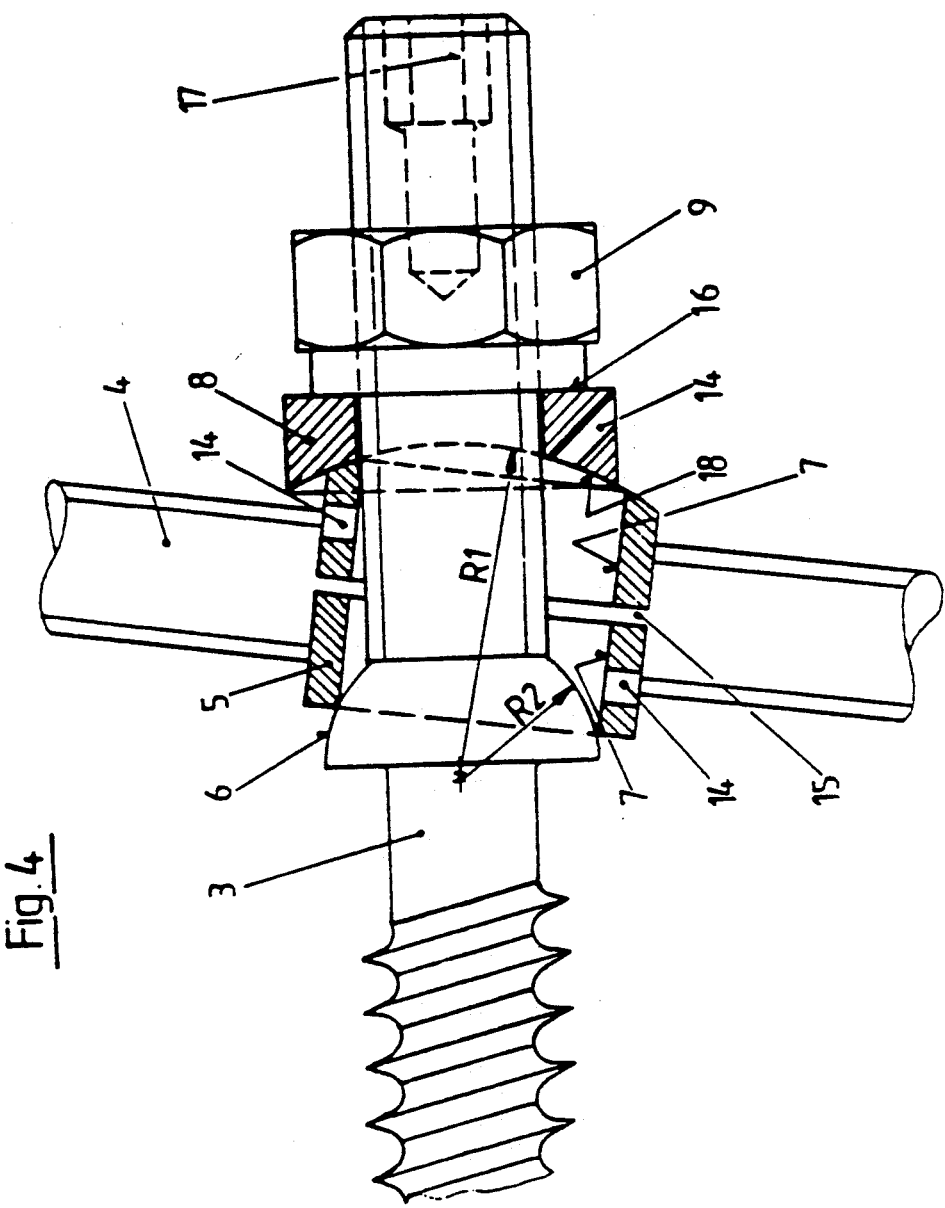

IMPLANT FOR VERTEBRAE WITH SPINAL STABILIZER

This invention relates to an implant for vertebrae. More particularly, this invention relates to an implant for fixing a pair of vertebrae relative to each other.

Heretofore, various types of instruments have been known for use in spinal surgery. For example, International application WO87/01026 describes a fixing instrument for spinal surgery which includes a unit having a pair of support members connected by means of a screw spindle and a plurality of securing members which are pivotally connected to the support members and which are intended to be secured to vertebrae by means of bone screws. French Patent 2,615,095 describes an implant for correcting scolioses which utilizes an elongated rod on which spaced apart brackets are mounted for holding bone screws in vertebrae. German Gebrauchsmuster G8816233.8 describes a template-like structure through which bone screws can be inserted into vertebrae. However, such instruments are rather cumbersome and not particularly useful for fixing the position of only two vertebrae.

Spondylodesis stabilizers have also been known for fixing the position of two vertebrae. Generally, these stabilizers are provided with a wide range of constructions. In this respect, the stabilizers aim to simultaneously satisfy partly contradictory requirements of an operating surgeon with a view to achieving an optimum solution. Assuming a serviceable fixed end position, the implants should be re-adjustable, be made of a small number of standard components, require no extensive preparation of the bone and be small and compact in relation to the vertebrae. German O.S. 2834891A1 describes a kit which is very flexible but which contains a large number of bulky mechanical elements in order to provide a stabilizer. A construction is described in Swiss Patent 646,857 which is much more compact but which requires the bone screws for a stabilizing element to be disposed in parallel planes to one another, at the latest, when a stabilization position is reached.

Other types of bone fixtures have also been know, such as described in European patent application 0240034 for fixation to sections of an elongated bone which has been fractured. However, these fixtures which include various pins to be threaded into a bone and which, in turn, are articulated within brackets mounted along a pair of rods, are not suited for fixing a pair of vertebrae.

Accordingly, it is an object of the invention to position the fixing elements of a spondylodesis stabilizer within a predetermined range of use and to permit an adjustment of a skew position of the elements prior to forming a rigid connection therebetween.

It is another object of the invention to be able to adjust a skew position of two fixing elements of a spondylodesis stabilizer without releasing the fixation of the elements in vertebrae.

It is another object of the invention to be able to place fixing elements in vertebrae in a skew position relative to each other while providing for a rigid connection of the fixing elements to a stabilizing element.

Briefly, the invention provides an implant for vertebrae which includes a pair of fixing elements for fixing in a pair of vertebrae, a stabilizing element interconnecting the fixing elements, clamps for securing each stabilizing element to a fixing element and means for articulating each clamp to a fixing element in order to permit pivoting of the clamp on the fixing element prior to securement of the stabilizing element to the fixing element.

The articulating means permits the stabilizing element to be fixed at any angle relative to a fixing element in a predetermined range prior to clamping to the fixing element.

Each clamp is provided with a pair of apertured portions which are disposed in spaced radial relation about a fixing element (e.g. a bone screw) while defining a slot-like incision therebetween. Each clamp is disposed about the stabilizing element for clamping of the stabilizing element thereon upon movement of the apertured portions toward each other.

In one embodiment, the articulating means includes a shoulder on a fixing element with a spherical surface received in an apertured portion of the clamp for pivoting of the clamp thereon. In addition, a flat washer is provided on the fixing element on an opposite side of the clamp from the shoulder to abut the clamp in slidable relation. A clamping nut is also threadably mounted on the fixing element and has a spherical surface received in the washer for pivoting of the washer thereon while the washer also slides relative to the clamp. In this embodiment, each fixing element can be initially mounted in a vertebrae in an intended position. Thereafter, with the clamp in a loose condition, the stabilizing element can be inserted into the clamp in a position to be clamped thereby. At this time, the stabilizing element can be pivoted relative to each fixing element via the clamp. In this way, two fixing elements may be disposed in a skew position relative to each other while the stabilizing element is articulated to each. Thereafter, the clamping nut on each fixing element is threaded so as to push the washer against the clamp causing the apertured portions of the clamp to move toward each other thereby clamping the stabilizing element.

In another embodiment, the articulating means includes a shoulder on the fixing element with a spherical surface received in the clamp for pivoting of the clamp thereon, a washer coaxially on the fixing element having a spherical surface slidably receiving a mating spherical surface of the clamp to permit pivoting of the clamp thereon and a clamping nut threadably mounted on the fixing element for pressing the washer against the clamp. This embodiment functions in a similar manner to the articulating means of the first embodiment. However, a pivoting action takes place between the washer and the clamp rather than a sliding motion.

The implant provides several advantages for an operating surgeon. Specifically, the surgeon can determine the position of the fixing elements in accordance with previous findings about the state of the vertebrae. The fixing elements may also be fitted without hinderance due to external members. Further, the surgeon can select and assemble a stabilizing element of minimal overall length adapted to the distance between the fixing elements and can make the connection rigid between the stabilizing elements and the fixing elements in a suitable position.

These and other objects and advantages of the invention will become more apparent from the following detailed description taken in conjunction with the accompanying drawings wherein:

FIG. 4 illustrates a view similar to FIG. 3 of a modified articulated arrangement in accordance with the invention.

Figure 1:
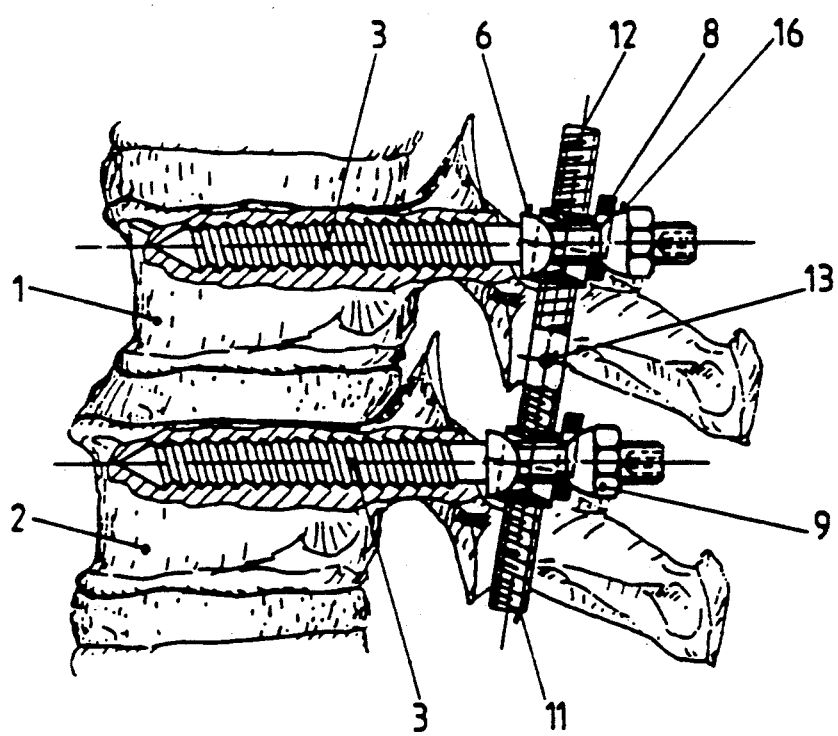
FIG. 1 illustrates a sectioned side elevational view showing a one-sided fixing of two vertebrae by means of an implant constructed in accordance with the invention.

Referring to FIG. 1, the implant for fixing two vertebrae 1, 2 together employs a pair of fixing elements in the form of bone screws 3 and a stabilizing element 4. As indicated, each bone screw 3 is screwed tightly into a respective vertebrae. To this end, as indicated in FIG. 3, each screw 3 has an internal hexagonal bore 17 at the free end to receive a suitable tool for screwing of the bone screw 3 into a vertebrae 1, 2.

Figure 2:
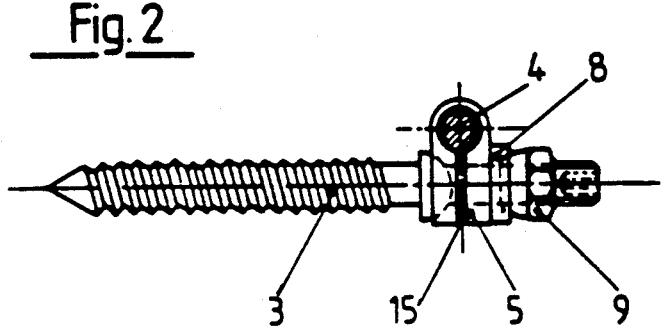
FIG. 2 illustrates a plan view of the implant of FIG. 1.
Figure 3:
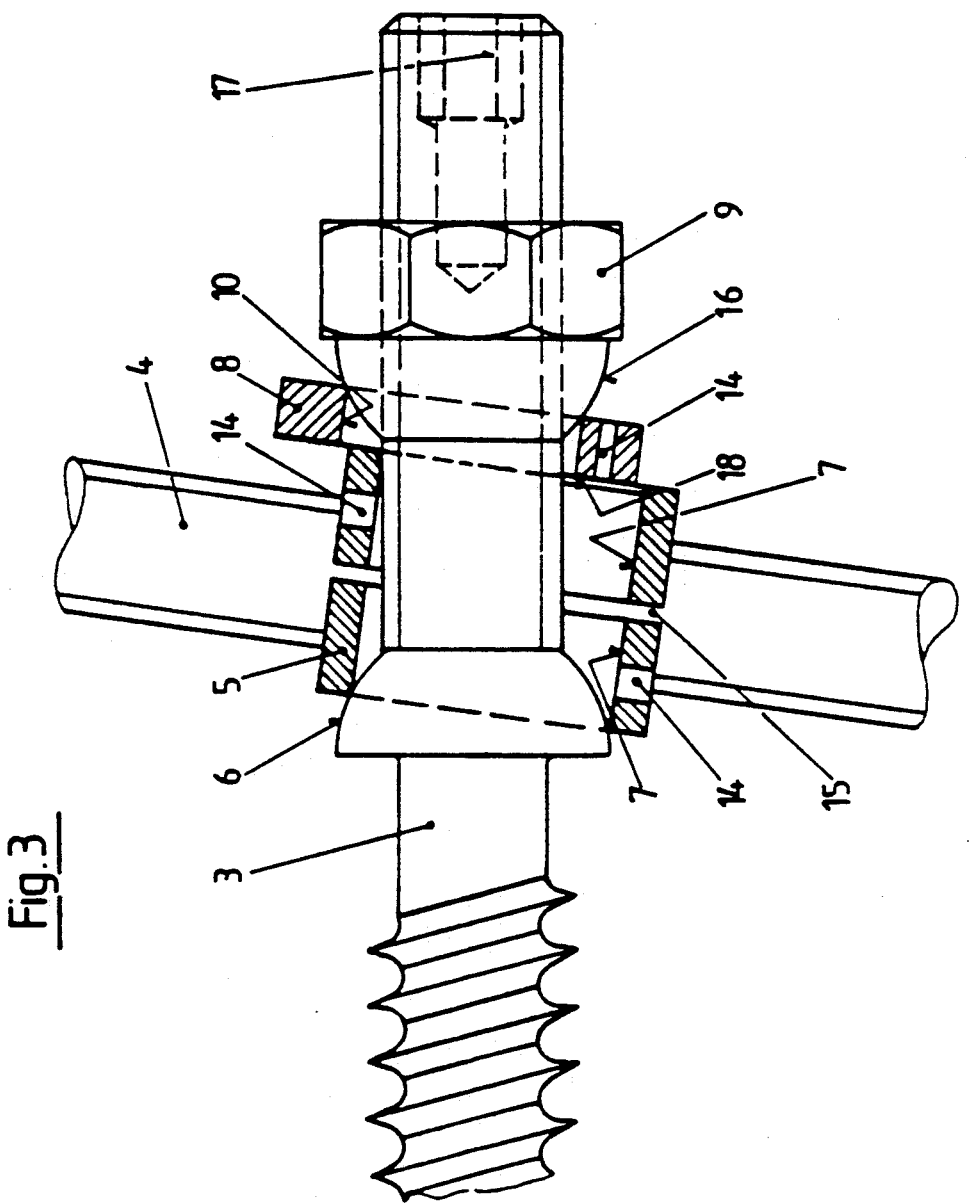
FIG. 3 illustrates an enlarged view of an articulated connection between a fixing element and the stabilizing element of the implant of FIG. 1.

Referring to FIGS. 2 and 3, the implant is provided with a pair of clamps 5 for securing the stabilizing element 4 to each respective bone screw 3. As illustrated, each clamp 5 has a pair of apertured portions which are disposed in spaced radial relation about a bone screw 3. In addition, the two apertured portions define a slot-like incision 15 therebetween. The clamp 5 is disposed about the stabilizing element 4 as indicated in FIG. 2 so as to clamp the stabilizing element 4 therein upon movement of the two apertured portions toward each other so as to close the incision 15. As illustrated in FIG. 3, each apertured portion of the clamp 5 has an aperture 7 which is of greater diameter than the diameter of the bone screw 3 passing therethrough.

As indicated in FIG. 2, each clamp 5 is provided with a tapped bore while the stabilizing element 4 is in the form a lead spindle having a left-hand thread 11 at the lower end, as viewed, and a right-hand thread 12 at the upper end. Thus, the stabilizing element 4 upon being rotated by a suitable tool, causes the two clamps 5 to be moved in opposite directions longitudinally of the stabilizing element 4. In addition, the stabilizing element 4 is provided with a bore 13 at a mid point so as to receive a wire (not shown) to secure the stabilizing element 4 against rotation.

Referring to FIGS. 1 and 3, a means is provided for articulating each clamp 5 on a bone screw 3 in order to permit pivoting of the clamp 5 on the bone screw 3 prior to securement of the stabilizing element 4 to the bone screw 3. This means includes a shoulder 6 on the bone screw 3 which has a spherical surface received in an aperture 7 of the clamp 5 for pivoting of the clamp 5 thereon. The shoulder 6 may be integrally formed with the bone screw 3 or otherwise fixed in place in any known manner. In addition, the articulating means includes a flat washer 8 which is disposed about the bone screw 3 in abutting slidable relation with the clamp 5 as well as a clamping nut 9 which is threadably mounted on a threaded portion of the bone screw 3. As indicated, the clamping nut 9 has a spherical surface 16 which is received within an aperture 10 of the washer 8 so as to permit pivoting of the washer 8 thereon while the washer 8 slides relative to the clamp 5.

Referring to FIG. 1, after the bone screws 3 have been fitted into the respective vertebrae 1, 2, the stabilizing element 4 is passed through the opened clamps 5. At this time, the clamps 5 may be pivoted on the shoulder 6 of each bone screw 3 into an inclined position. Thereafter, each clamping nut 9 is rotated so as to press the washer 8 against the clamp 5 so as to transmit a clamping force thereon. As indicated in FIG. 3, the washer 8 has a contact surface 18 which takes up the inclination of the clamp 5 while the outside edge of the internal bore 10 follows the spherical convex surface 16 of the clamping nut 9. Upon clamping being achieved, the clamp 5 is mounted in the inclined position and the washer 8 takes up a parallel position relative to the clamp 5. At the same time, the apertured portions of the clamp 5 are brought together between the shoulder 6 and clamping nut 9 so as to clamp the stabilizing element 4 therein. As indicated, the axis of the stabilizing element 4 is skew to the axis of each bone screw 3. That is, the longitudinal axis of the stabilizing element 4 is spaced from the longitudinal axis of each screw 3 in a non-intersecting manner.

In the event that a re-adjustment is required, the stabilizing element 4 can be rotated so as to adjust the two bone screws 3 relative to each other, for example, to bring about a re-alignment of the vertebrae 1, 2.

A self-locking of the clamping occurs when the application of the clamping force produces substantial adhesion forces in the contact surfaces between the washer 8 and clamp 5 that even an externally initiated reduction of the inclination of the clamp 5 is prevented.

Alternatively, it may be possible to assemble the implant prior to threading of the bone screws 3 into the vertebrae 1, 2. In this condition, the stabilizing element 4 would be threaded into the clamps 5 in an unclamped manner. Each bone screw 3 can be rotated relative to the clamp 5 in view of the enlarged apertures 7 of the clamp portions as indicated in FIG. 3.

The implant provides two superimposed adjustment zones. First, rotation of a clamp 5 on the helix line of the stabilizing element 4 may be performed independently until clamping. Second, the inclined position of the rear part of the bone screw 3 can be adjusted in a clamp aperture 7. Theoretically, it would be sufficient to pin the washer 8 to the clamp 5 in the resulting inclined position in order to prevent displacements in the common boundary between the surfaces of the clamp 5 and washer 8 and to ensure self-locking of the connection in the inclined position. For practical use and simplicity of correction of the adjustment, it is preferred to increase the friction in the boundary surfaces between the washer 8 and clamp 5. This increase can be provided by a choice of material, of surfaces and/or by roughening the surfaces and/or by a meshing structure of the surfaces.

Referring to FIG. 4, the means for articulating the clamp 5 to a bone screw 3 may include a shoulder 6, as above, a washer 8 having a spherical surface 18 slidably receiving a mating spherical surface of the clamp 5 to permit pivoting of the clamp 5 thereon and a clamping nut 9 having a flat contact surface 16 for abutting the washer 8. As indicated, the mating contact surfaces 18 of the washer 8 and clamp 5 are disposed on a common radius R1 and, when assembled without inclination, the common surfaces have substantially the same center as the spherical surface on the shoulder 6. As indicated, the spherical surface on the shoulder 6 has a smaller radius R2.

The contact surface 16 of the clamping nut 9 on the washer 8 is in the form of an axial pressing shoulder and the washer 8 is centered relative to the bone screw axis. The mating contact surfaces 18 of the washer 8 and clamp 5 may also be roughened in order to increase the frictional force therebetween.

The connection between the stabilizing element 4 and each bone screw 3 is self-lockingly rigid in every pivotable inclined position. This is advantageous for the operating surgeon. To this end, the pivotable clearance of the bone screw 3 in the apertures 7 of the clamp 5 is so small that the friction which occurs in the contact surface 18 has a self-locking effect. In addition, the hexagonal bore 17 in the bone screw 3 may continue as a blind bore so that, by means of a push tool, a bending moment affecting the inclined position can be applied to the bone screw 3 when the nut 9 is being tightened.

As illustrated in FIGS. 3 and 4, each of the clamps 5 and the washers 8 is formed with bores 14 to facilitate a more direct connection between the external surfaces and the internal surfaces in order to obviate "dead" spaces not participating in the metabolism. For example, each clamp 5 is provided with a plurality of radial bores 14, each flat washer 8 is provided with an axial bore 14 and each part-spherical washer 8, as shown in FIG. 4, is provided with an inclined bore 14.

The invention thus provides an implant which permits bone screws to be positioned within a predetermined range of use corresponding to the fixing possibilities of the vertebrae. In addition, the bone screws may be placed skew to one another with the implant permitting an adjustment of the skew position during an adjustment of the stabilizing element. The clamps of the implant also insures a rigid connection of one bone screw to the other after the end position has been reached.

What is claimed is:

1. In an implant for vertebrae, the combination comprising
    a fixing element having a longitudinal axis for fixing in a vertebrae;
    a stabilizing element having a longitudinal axis for interconnecting a pair of said fixing elements;
    a clamp for securing said stabilizing element to said fixing element with said axes spaced from each other in a non-intersecting manner, said clamp having a bore receiving said stabilizing element and a pair of apertured portions offset from said bore and receiving said fixing element in spaced radial relation; and
    means for articulating said clamp on said fixing element to permit pivoting of said clamp on said fixing element into an inclined position relative to said axis of said fixing element prior to securement of said stabilizing element to said fixing element while maintaining said inclined position after securement of said stabilizing element to said fixing element.

2. The combination as set forth in claim 1 wherein said pair of apertured portions define a slot-like incision therebetween.

3. The combination as set forth in claim 2 wherein said means includes a shoulder on said fixing element having a spherical surface received in said clamp for pivoting of said clamp thereon, a flat washer on said fixing element abutting said clamp in slidable relation and a clamping nut threadably mounted on said fixing element and having a spherical surface received in said washer for pivoting of said washer thereon while sliding relative to said clamp.

4. The combination as set forth in claim 3 wherein said clamp has at least one radial bore therein.

5. The combination as set forth in claim 3 wherein said washer has at least one axial bore therein.

6. The combination as set forth in claim 2 wherein said means includes a shoulder on said fixing element having a spherical surface received in said clamp for pivoting of said clamp thereon, a washer on said fixing element having a spherical surface slidably receiving a mating spherical surface of said clamp to permit pivoting of said clamp thereon and a clamping nut threadably mounted on said fixing element for pressing said washer against said clamp.

7. The combination as set forth in claim 6 wherein said clamp has at least one radial bore therein.

8. The combination as set forth in claim 6 wherein said washer has at least one bore therein.

9. The combination as set forth in claim 7 wherein said bore of said clamp is a tapped bore and said stabilizing element has a threaded end received in said bore.

10. An implant for vertebrae comprising
    a pair of fixing elements for fixing into a pair of vertebrae;
    a stabilizing element for interconnecting said fixing elements;
    a pair of split clamps, each clamp having a pair of apertured portions mounted on a respective fixing element and disposed in spaced relation to define a slot-like incision therebetween, each clamp being disposed about said stabilizing element for clamping on said stabilizing element upon movement of said apertured portions toward each other;
    a shoulder on each fixing element having a spherical surface received in a respective apertured portion of a respective clamp to permit pivoting of said respective clamp thereon into an inclined position relative to said respective fixing element;
    a washer mounted on each fixing element on a side of a respective clamp opposite said shoulder; and
    a clamping nut threadably mounted on each respective fixing element for pressing a respective washer against a respective clamp to move said apertured portions of said respective clamp together while holding said clamp in an inclined position.

11. An implant as set forth in claim 10 wherein each said clamping nut has a spherical surface received in a respective washer to permit pivoting of said washer thereon prior to movement of said portions of a respective clamp toward each other.

12. An implant as set forth in claim 11 wherein each said washer is flat.

13. An implant as set forth in claim 10 wherein each washer has a spherical surface in contact with a mating spherical surface on a respective clamp to permit pivoting of said clamp relative to said washer.

14. An implant as set forth in claim 10 wherein at least one of said washers and one of said clamps has a roughened surface facing the other to increase a frictional force therebetween.

15. An implant as set forth in claim 10 wherein at least one of said washers and said clamps has a bore passing therethrough to communicate an interior thereof to the exterior thereof.

16. An implant as set forth in claim 1 wherein said stabilizing element has a left-hand thread on one end and a right-hand thread on an opposite end and each said split clamp being threaded onto a respective end of said stabilizing element whereby rotation of said stabilizing element causes said clamps to move in opposite directions.

17. An implant for vertebrae comprising a pair of bone screws for fixing into a pair of vertebrae, each screw having a longitudinal axis;

a stabilizing element for interconnecting said screws, said element having a left-hand thread at one end and a right-hand thread at an opposite end;

a pair of split clamps, each clamp having a tapped bore receiving a respective end of said stabilizing element in threaded relation and a pair of longitudinally spaced apertured portions receiving a respective bone screw therein in spaced radial relation with said bone screw on an axis disposed in non-intersecting relation to said stabilizing element, said portions being movable towards each other to effect clamping of said element in said bore; and means for articulating each clamp on a respective bone screw to permit pivoting of said respective clamp on said respective bone screw prior to clamping of said stabilizing element to said bone screws.

* * * * *

UNITED STATES PATENT AND TRADEMARK OFFICE
CERTIFICATE OF CORRECTION

PATENT NO. : 5,084,048
DATED : January 28, 1992
INVENTOR(S) : Jacob et al.

It is certified that error appears in the above-identified patent and that said Letters Patent is hereby corrected as shown below:

Column 1, line 43, change "know," to --known,--

Column 3, line 35, change "form" to --form of--

Column 6, line 14, change "7" to --1--

Signed and Sealed this

Seventeenth Day of August, 1993

Attest:

BRUCE LEHMAN

Attesting Officer

Commissioner of Patents and Trademarks